United States Patent
Weidmann (10) Patent No.: US 9,656,456 B2
(45) Date of Patent: May 23, 2017

(54) MACHINE AND METHOD FOR PRINTING MATERIAL WEBS

(75) Inventor: Bjoern Weidmann, Osnabrueck (DE)

(73) Assignee: WINDMOELLER & HOELSCHER KG, Lengerich (DE)

(*) Notice: Subject to any disclaimer, the term of this patent is extended or adjusted under 35 U.S.C. 154(b) by 0 days.

(21) Appl. No.: 14/238,538

(22) PCT Filed: Aug. 17, 2012

(86) PCT No.: PCT/EP2012/066085
§ 371 (c)(1),
(2), (4) Date: Feb. 12, 2014

(87) PCT Pub. No.: WO2013/026792
PCT Pub. Date: Feb. 28, 2013

(65) Prior Publication Data
US 2014/0190362 A1    Jul. 10, 2014

(30) Foreign Application Priority Data

Aug. 22, 2011 (DE) .......... 10 2011 110 800
Apr. 3, 2012 (DE) .......... 10 2012 205 482

(51) Int. Cl.
*B41F 21/00* (2006.01)
*B41F 33/00* (2006.01)
(Continued)

(52) U.S. Cl.
CPC .......... *B41F 21/00* (2013.01); *B41F 33/0036* (2013.01); *B41F 33/02* (2013.01); *G01N 21/8983* (2013.01); *G01N 2021/8825* (2013.01)

(58) Field of Classification Search
CPC . B41F 21/00; B41F 33/0036; G06K 9/00442; G06K 9/036; G06T 2207/30144; B41J 11/0085
See application file for complete search history.

(56) References Cited

U.S. PATENT DOCUMENTS 3,942,230 A * 3/1976 Nalband .......... 492/53
4,967,663 A * 11/1990 Metcalf .......... 101/348
(Continued)

FOREIGN PATENT DOCUMENTS

DE    43 21 177    1/1995
DE    196 13 084    10/1997
(Continued)

OTHER PUBLICATIONS

Boppe, et al., Machine Translation of DE 102004007374, original publication date Aug. 4, 2005.*

*Primary Examiner* — David Banh
(74) *Attorney, Agent, or Firm* — Jacobson Holman, PLLC.

(57) ABSTRACT

The invention describes a machine for printing material webs (4), which comprises a station (1, 11, 41) for monitoring the printed material web (4), with the station (1, 11, 41) for monitoring the material web (4) comprising a sensor (3, 13) for monitoring the web (4) and at least one counter support (2, 12) for guiding the web (4), with at least one counter support (2, 12) being located on the side of the web (4) facing away from the sensor (3, 13).
The invention is characterized by a device for providing blow air, which shows jets (6, 7) extruding blow air in the area of the station (1, 11, 41) for monitoring the material web (4) at the side of the material web (4) facing the sensor (3, 13).

16 Claims, 7 Drawing Sheets

(51) Int. Cl.
    *B41F 33/02*     (2006.01)
    *G01N 21/898*     (2006.01)
    *G01N 21/88*     (2006.01)

(56) References Cited

U.S. PATENT DOCUMENTS

| | | | | |
|---|---|---|---|---|
| 5,598,006 | A * | 1/1997 | Stringa | 250/559.46 |
| 5,724,437 | A | 3/1998 | Bucher et al. | |
| 5,774,225 | A * | 6/1998 | Goldstein et al. | 356/402 |
| 5,809,885 | A * | 9/1998 | Koch et al. | 101/232 |
| 6,176,482 | B1 * | 1/2001 | Reinhard et al. | 271/227 |
| 6,328,440 | B1 * | 12/2001 | Medin et al. | 347/102 |
| 2001/0039892 | A1 * | 11/2001 | Frossard et al. | 101/228 |
| 2003/0005841 | A1 * | 1/2003 | Riepenhoff | B41F 33/0045 101/484 |
| 2003/0024301 | A1 * | 2/2003 | Graeffe | G01B 11/0691 73/37.6 |
| 2003/0035870 | A1 * | 2/2003 | Ackley et al. | 426/383 |
| 2004/0000652 | A1 * | 1/2004 | Guha et al. | 250/559.45 |
| 2004/0173113 | A1 * | 9/2004 | Dunninger et al. | 101/408 |
| 2005/0095046 | A1 * | 5/2005 | Beehler | 400/23 |
| 2006/0096476 | A1 * | 5/2006 | Boppel | B41F 13/02 101/228 |
| 2007/0008538 | A1 * | 1/2007 | Kiraly | 356/430 |
| 2007/0139703 | A1 * | 6/2007 | Shimamura et al. | 358/1.15 |
| 2013/0003063 | A1 * | 1/2013 | Headley et al. | 356/402 |
| 2014/0049590 | A1 * | 2/2014 | Tateishi et al. | 347/104 |
| 2014/0077081 | A1 * | 3/2014 | Ohama | 250/338.1 |
| 2014/0077101 | A1 * | 3/2014 | Ohama | 250/461.1 |
| 2014/0083915 | A1 * | 3/2014 | Nakada | 209/552 |
| 2014/0190362 | A1 * | 7/2014 | Weidmann | 101/407.1 |
| 2014/0208970 | A1 * | 7/2014 | Weidmann | 101/417 |

FOREIGN PATENT DOCUMENTS

| | | |
|---|---|---|
| DE | 10 2004 007 374 | 8/2005 |
| DE | 10 2007 025 910 | 12/2008 |

* cited by examiner

MACHINE AND METHOD FOR PRINTING MATERIAL WEBS

CROSS-REFERENCE TO RELATED APPLICATION

This is a national stage of PCT/EP12/066085 filed Aug. 17, 2012 and published in German, which has a priority of German no. 10 2011 110 800.2 filed Aug. 22, 2011, and a priority of German no. 10 2012 205 482.0 filed Apr. 3, 2012 hereby incorporated by reference.

BACKGROUND OF THE INVENTION

1. Field of Invention

The invention relates to a machine and a method for printing material webs as described herein.

2. Description of the Prior Art

Printed materials are examined in order to check the printing results. Generally, for this purpose a finished printed product is removed and examined for its optical impression, among other things. Recently, printed material webs are increasingly observed inline via sensors, such as cameras, in order to continuously monitor the result of the printing process and to come to a conclusion faster. DE 10 2004 007 374 B3 also shows a device for the inline web monitoring. In this publication the web to be examined is guided by a counter support in the area of the web observation station. Here, the counter support is positioned on the side of the web facing away from the sensor. The counter support shows a porous or perforated surface through which air is pressed. As a consequence of this measure an air pocket forms, on which the web glides.

Experience has shown that measuring errors occur in the inline web observation stations shown above. This particularly applies when color impressions of transparent or partially transparent printed materials are examined. Additionally, some opaque materials may be problematic, here.

SUMMARY OF THE INVENTION

Therefore, the objective of the present invention is to reduce these measuring errors using a machine and a method as described herein.

Accordingly, devices are provided which generate a pressure difference, which are implemented such that a force affecting the web in the direction towards the counter support results, with a first device, arranged at the side of the web facing the sensor, generating a pressure, and/or a second device, arranged at the side of the web facing away from the sensor, generating a vacuum.

Compared to prior art, it is particularly not provided to guide the material web contact-free over the counter support. Rather, devices are provided by which the material web is pressed onto and/or against the counter support. In a first embodiment of the invention, blowing air is used in order to press the material web onto and/or against the counter support. An advantageous alternative or complementary option to achieve this comprises applying a vacuum to the side of the material web facing away from the sensor and thus suctioning it against the counter support.

For this purpose the counter support must be provided with appropriate suction apertures or the like. Suction or vacuum devices must also be provided. The disadvantages of a vacuum include that any misalignment of the web naturally leads to a complete opening of the vacuum jets to the environment, which may result in a rapid loss of vacuum. Furthermore, any change of the web format (change of the width of the web) makes an adjustment of the vacuum jets necessary (vacuum jets need to be closed for narrower webs and vice versa).

Both the use of a vacuum as well as the use of blow air leads to a compression of the web against the counter support. It is interesting that the web seems to initially show a certain resistance against the "compression," which increases with the traveling speed of the web. This circumstance might be explained with the laminar air flow, which is entrained by the web when traveling. Once this resistance has been overcome and the web falls short of a certain distance from the counter support, the Bernoulli effect applies between the web and the counter support and leads to a further approach of the web towards the counter support. It is possible and in many cases advantageous to reduce the distance to a range of one millimeter or even less (<0.5 mm, <0.2 mm, actually preferably <0.1 mm or <0.05 mm, etc.)

The quality of testing the printed web is improved by the reduction of the distance between the web and the counter support. This particularly applies for measurements of the color location and the like. Such measurements are advantageously performed using spectral-photometrical measuring sensors.

In another variant according to the invention, a second device is provided which is arranged at the side of the web facing away from the sensor. This device generates a vacuum at the aforementioned side of the web.

It is particularly advantageous for the second device also to comprise a device showing jets with which blow air can be provided. This blow air advantageously shows a flow rate which is faster than the traveling speed of the web. This flowing blow air can quasi generate an airflow by which the web is pulled towards the counter support, utilizing the Bernoulli effect. This variant shows particular advantages in reference to an embodiment with suction openings, because considerably less energy is required. For embodiments with suction apertures, false air is frequently suctioned, i.e. environmental air, so that frequently a higher pump capacity is required then theoretically foreseen. Additionally, the vacuum develops very slowly in a variant with suction apertures. However, the material web is pulled very quickly against the counter support when using an embodiment according to the invention.

In a particularly effective embodiment, the jets are arranged in directions perpendicular in reference to the travel direction (z) so that the blow air assumes a direction of flow which extends essentially perpendicular in reference to the travel direction of the material web.

In this case a particularly strong effect is observed so that the web is also pulled against the counter support at a comparatively slow flow rate.

In order to allow a progression of the material web that as straight as possible, it is advantageous for the jets to be arranged in channels extending in the counter support, which are aligned perpendicularly in reference to the travel direction of the material web. These channels on the lateral faces of the counter support are preferably open so that the flowing, pressurized air can escape.

In another embodiment of this variant of the invention, the jets are arranged in the center of the channels such that they generate flow in a direction towards the side of the counter support. In this case all areas of the web, particularly the edge regions, are evenly pulled towards the counter support.

Particularly in this context an even and/or white surface of the counter support is advantageous.

Due to the fact that friction may develop between the web and the counter support it is advantageous for the area of the counter support, which can come into contact with the web, to extend only over a portion of the width of the web. In this case it is advantageous for the counter support to be displaceable in this direction. This may occur by fastening the counter support in a displaceable fashion on a sled on a traverse.

It is advantageous to provide at least one second sensor in the immediate proximity of the first sensor and the first counter support. Using this at least one second sensor, other parameters can be measured than with the first sensor. This is advantageous for the following reasons and leads to a further improvement of the quality of measurements with the at least one additional sensor:

The first sensor can be triggered by the second sensor. This has particular advantages when the at least one first sensor is a spectra-photometric sensor and the at least one second sensor is an imaging sensor. In addition to triggering, for example, an orientation of the first sensors in the x-z plane can then also be given. The short distance between the first and the second sensors reduces imprecisions, for example by an alternating web stretching. Accordingly it is advantageous if only one guide roller or none at all is located on the web traveling path between the measuring points of at least one first and at least one second sensor.

Due to the other measuring parameters, which shall be measured by at least one second sensor, the desired distance between the web and the second counter support may be completely different than the one between the web and the first counter support. Here, air pockets and rollers may once more be used advantageously.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
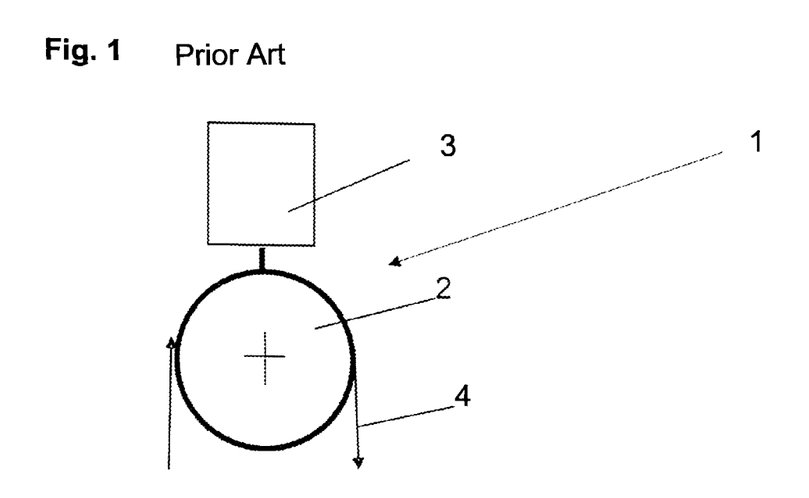
FIG. 1 A station for monitoring a material web according to prior art
Figure 2:
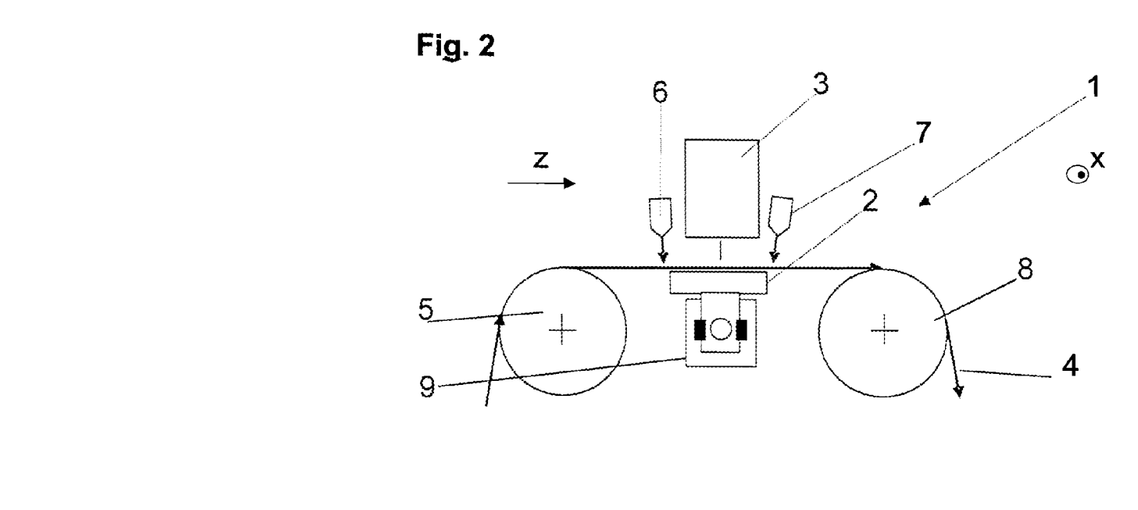
FIG. 2 A station with a first sensor and a first counter support

FIG. 1 shows a station 1 for monitoring a material web 4 according to prior art, in which a non-transparent web material travels on a black rubber roller 1, which serves as a first counter support 2, and is guided past a first sensor 3. In transparent web materials, white rollers should actually be used. However, they are expensive, become soiled very easily, and thus they are not practical. FIG. 2 shows a station 1 for monitoring a material web 4 in a machine according to the invention. In this station 1 the web first travels first over the master roller 5, provided with a rotary pulse generator, not shown, into the station 1. Subsequently, the web is influenced by the compressed air jet 6, which emits compressed air pressing the web 4 in the direction towards the counter support 2. In the proximity of this first counter support 2 the first sensor 3 performs its measurements. Another influencing area of a compressed air jet is located downstream in reference to the counter support 2, namely the compressed air jet 7. The web 4 leaves this station 1 via the guide roller 7. The counter support 2 may be embodied like tiles. It may be displaced with the help of a traverse 9 into the correct position in the x-direction of the web 4 (width). Additionally, the exchange of one tile is possible easily and cost-effectively. An automatic test for soiling can also occur easily and quickly due to the small area in question, because the tile can be moved out of the proximity of the printed material 4 and be measured there. This would not be possible with a roller. When measuring transmissive and/or transparent materials, the air gap between the printed material and the measuring background is of decisive importance for the quality of measurements. Simultaneously, any permanent contacting of the printed material with the background should be avoided.

For this reason, the solution provides that the measuring background 2 is located slightly below the printed material 4 guided by two rollers 5, 8. For the measurement, the material is blown via pressurized air jets 6, 7 against the measuring background 2. The jets are located in the travel direction z of the web shortly upstream and downstream of the measuring background. This way, the entrained air is scraped off at the edges of the measuring background and the air gap is reduced to a minimum. Based on the Bernoulli effect, the web is suctioned towards the background better and better with increasing traveling speed. The pressure of the compressed air can furthermore be adjusted to the material features, web tension, and web speed. After the measuring process has been concluded, the compressed air is shut off so that the web 4 once more moves freely.

The web 4 could also be suctioned to the measuring background 2 by a vacuum. This solution however leads to problems when measuring near the edge of the web, because here only insufficient vacuum can form for suctioning the web 4. When using compressed air this is irrelevant.

Figure 3:
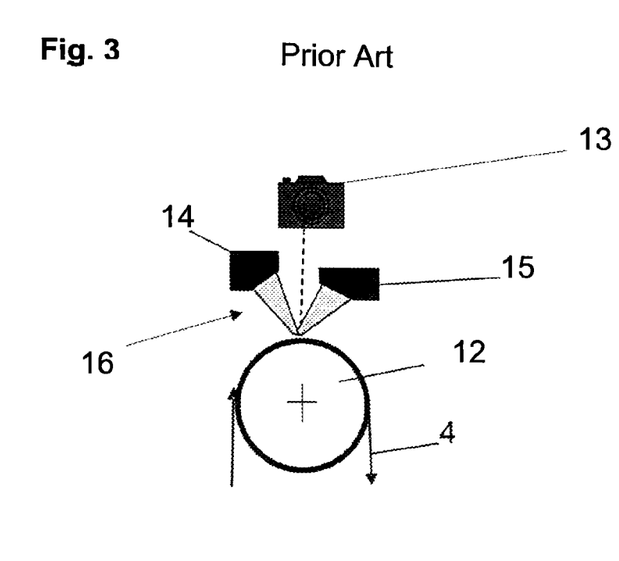
FIG. 3 A second station for monitoring a material web according to prior art
Figure 4:
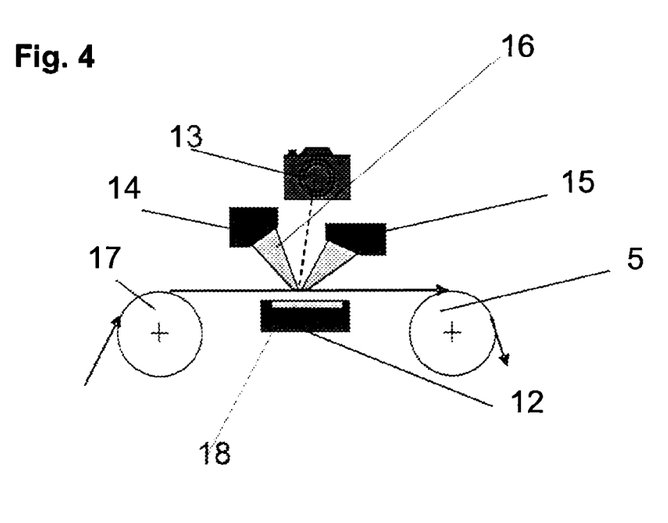
FIG. 4 A station with a second sensor and a second counter support

FIG. 3 shows a simple second station 11 for monitoring a material web, as sometimes used in prior art for imaging sensors 13. The web progression is the same as in FIG. 1. Here, a white roller 12 is used as the measuring roller (with the requirements not being as high as during color measurements). The disadvantages of such a method include that white objects cannot be detected on transparent materials. Here, the bright field 14 and the dark field 15 illumination are to be mentioned, with their light cones 16 also being shown. FIG. 4 shows a second station 11, in which the guiding of the web 4 is performed by the guide roller 17 and the master roller 5. The counter support 12, or preferably the measuring background does not contact the web 4. However, this counter support is equipped with a background illumination 18 such that the camera 13 can here also detect the "white eagle on a white background."

Figure 5:
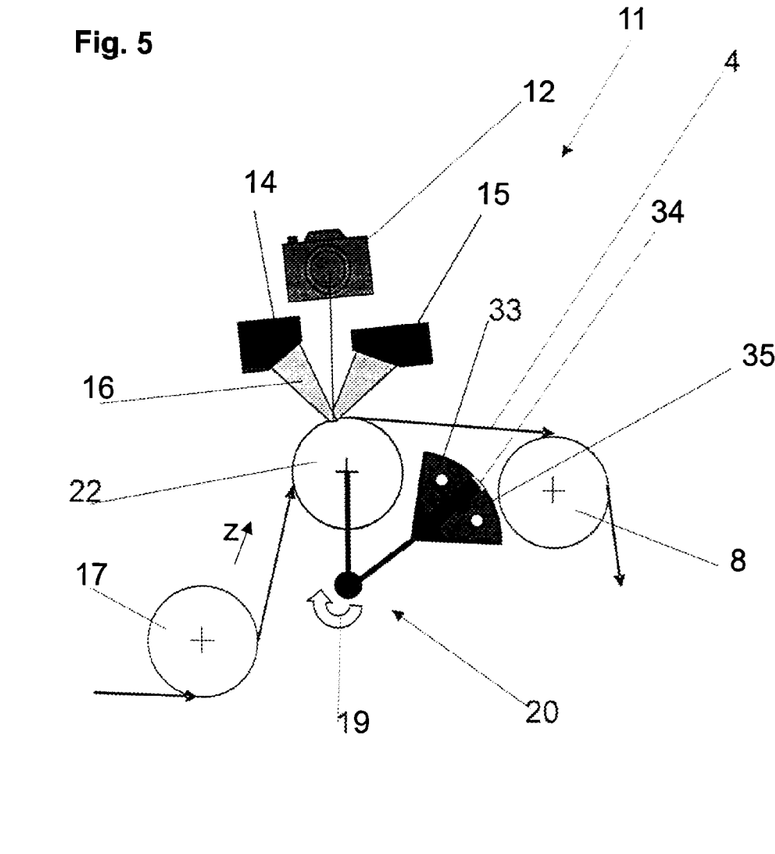
FIG. 5 Another station with a second sensor and a second counter support
Figure 6:
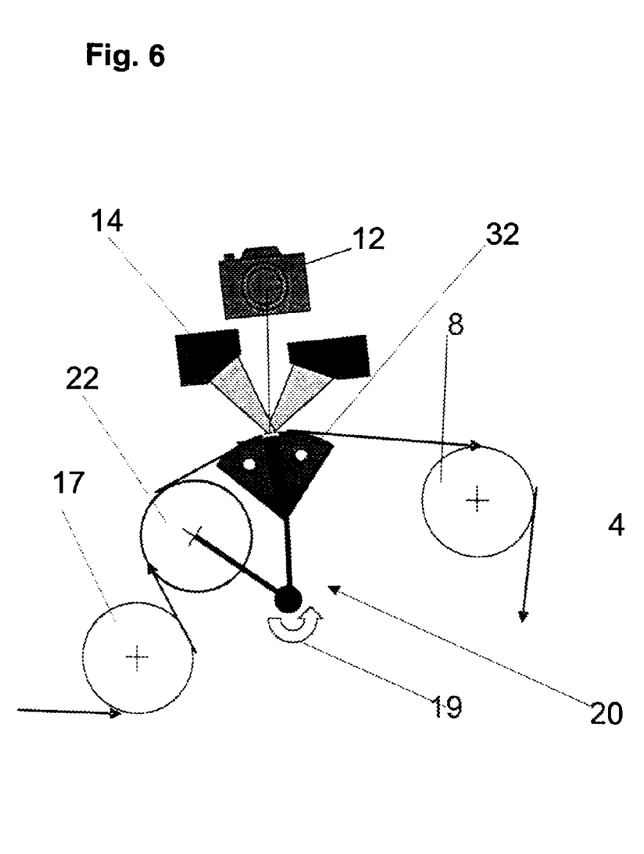
FIG. 6 The station from FIG. 5 in a different operating mode

FIGS. 5 and 6 show another second station 11 for monitoring a material web 4. This station comprises a counter support system 20 with two alternative counter supports 22 and 32. In FIG. 5 one white roller 22 serves as the counter support and/or the measuring background. The arrow 19 indicates that the system 20 can also activate the counter support 32 within the scope of a pivotal motion, as shown in FIG. 6. Here, the roller 22 only serves as a guide roller, while the counter support 32 guides the web on the side opposite the sensor.

Figure 7:
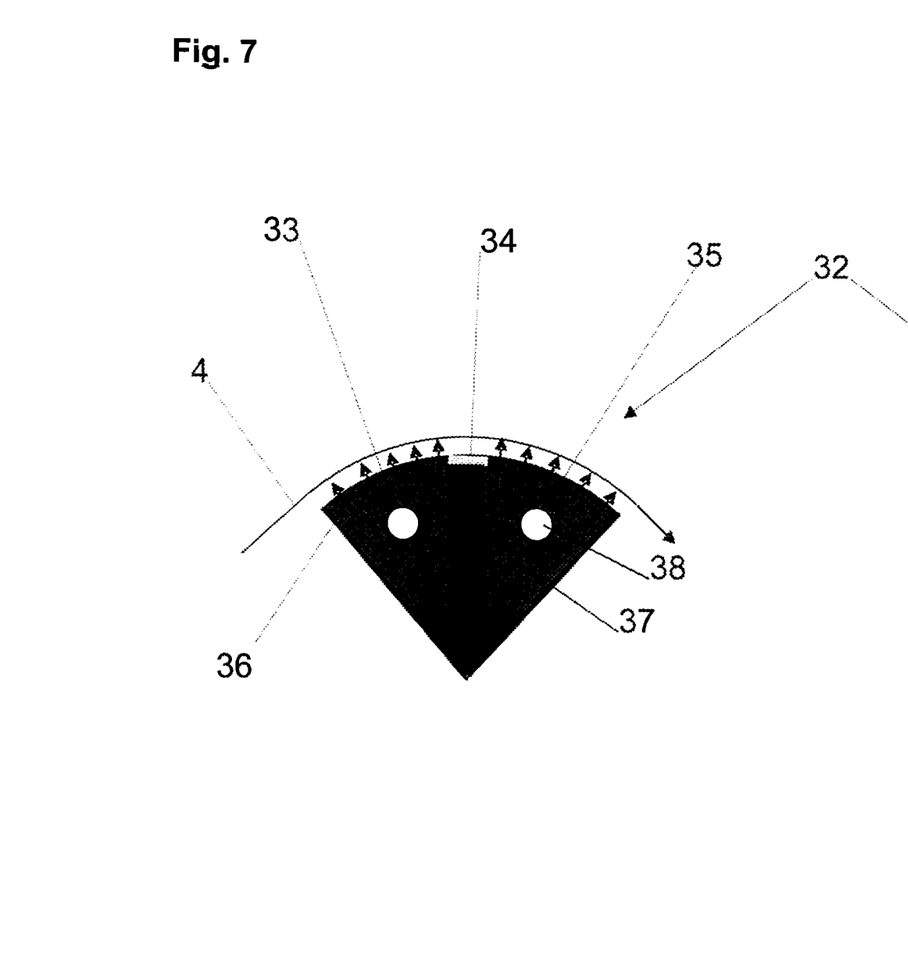
FIG. 7 A cross-sectional illustration of an advantageous second counter support
Figure 8:
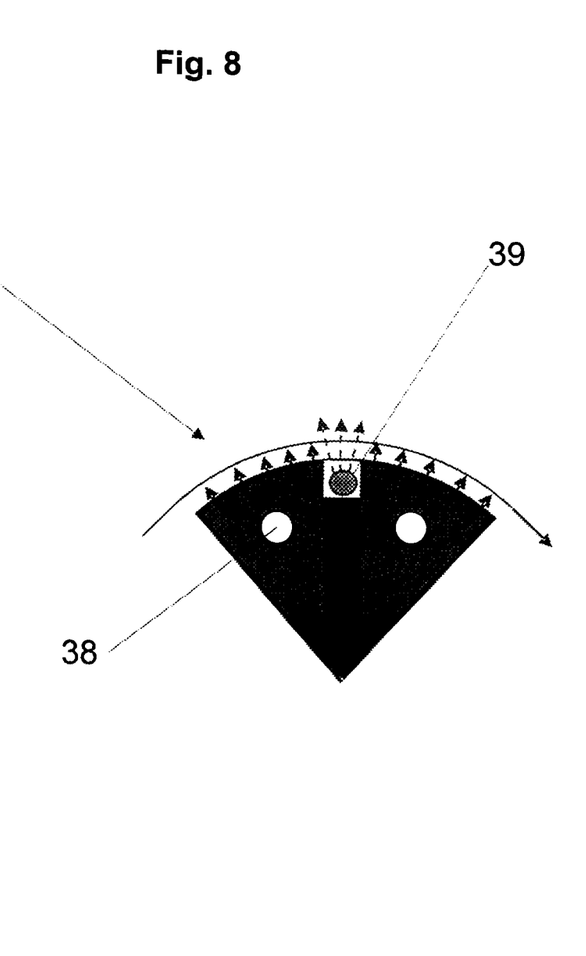
FIG. 8 A cross-sectional illustration of another advantageous second counter support, FIG. 9 A station with a first and a second sensor and a first and a second counter support FIG. 10 A station with a device generating a vacuum FIG. 11 Another station with a device generating a vacuum FIG. 12 A view A-A of FIG. 10

FIGS. 7 and 8 show two exemplary embodiments for this counter support 32. The surface of the counter support 32 facing the web 4 shows a convex profile. In the travel direction z, the web 4 first travels over the first surface 33 of the counter support 32. It is made from a porous material, preferably micro-porous Teflon, which can be produced by a sintering process. This material is penetrated by a pipe 38, which introduces compressed air. This compressed air flows through the porous material and exits, as shown by the arrows 36, at the first surface 33 of the porous material. Here, an air pocket forms, which is illustrated by the arrows 36, and floats above the web 4. Then, moving in the travel direction z, the web reaches the proximity of the reflector 34, which may replace a background illumination 18, 39. The measure of using a reflector 34 as the measuring background has proven so advantageous that this measure is beneficial, even independent from the remaining design of the measuring station, and perhaps deserves patent protection.

Figure 9:
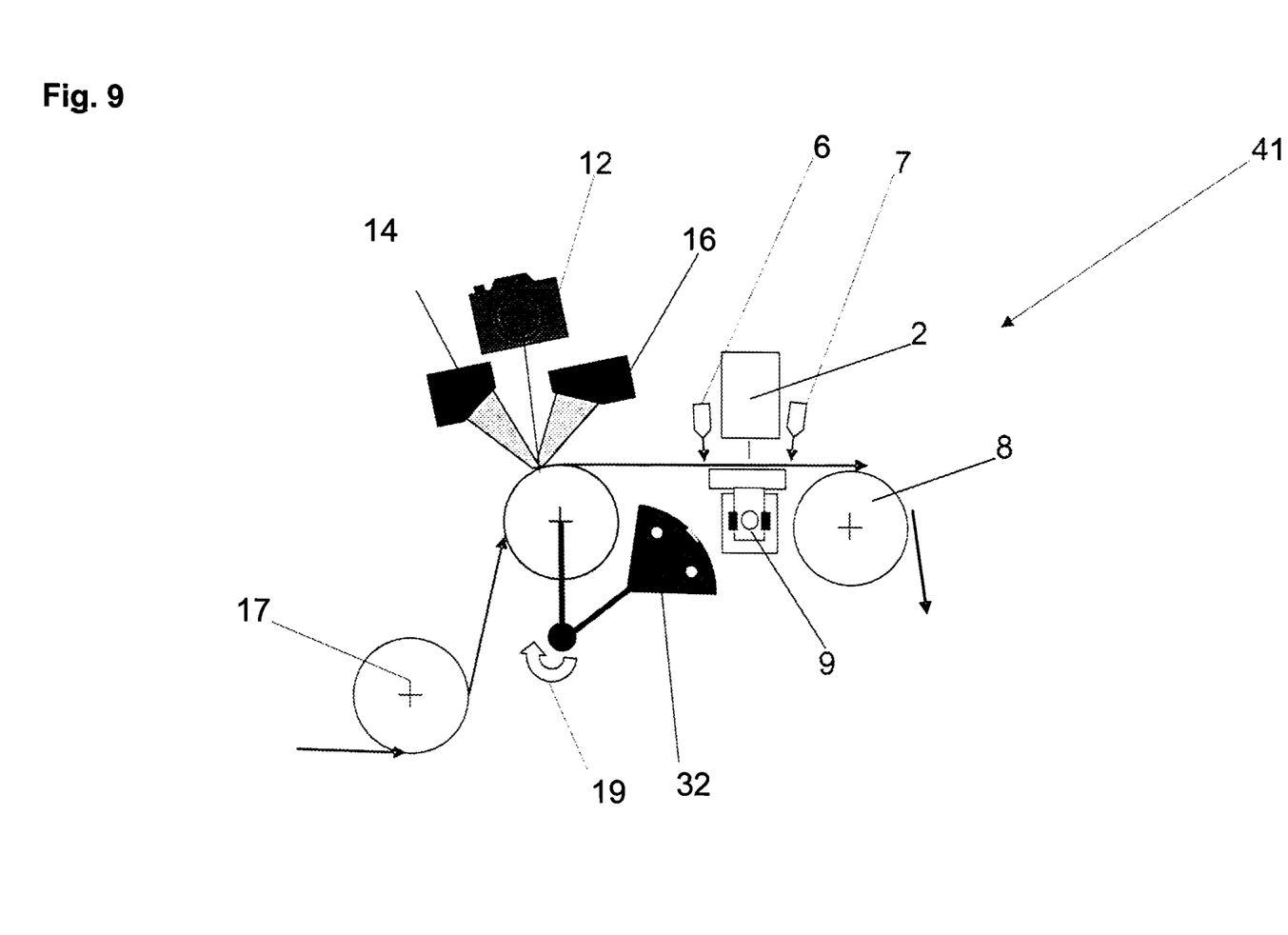

The second surface 35 of the counter support 32 is arranged downstream in the travel direction z of the web in reference to the reflector 34, designed as a mirror image of the first surface 33 of the counter support 32. The counter support 32 shows a pressure-resistant housing 37 on the sides facing away from the web 4, preventing any escape of compressed air. The counter support 32 in FIG. 8 shows, instead of the reflector 34, a background illumination 39 and is otherwise designed identical to the counter support 32 shown in FIG. 7. FIG. 9 shows a station 41, which combines the functional components of the station 11 of FIG. 5 with the functional components of station 1 of FIG. 2.

As already mentioned, this arrangement in one station provides additional advantages for the quality of the measurement. In case of multi-color printing machines it is advantageous to provide one of the stations 1, 11, 41 shown downstream in reference to the last printing device. The use of compressed air jets 6, 7 also leads to a cleaning of the web 4 and the optic elements of the web monitoring station.

Figure 10:
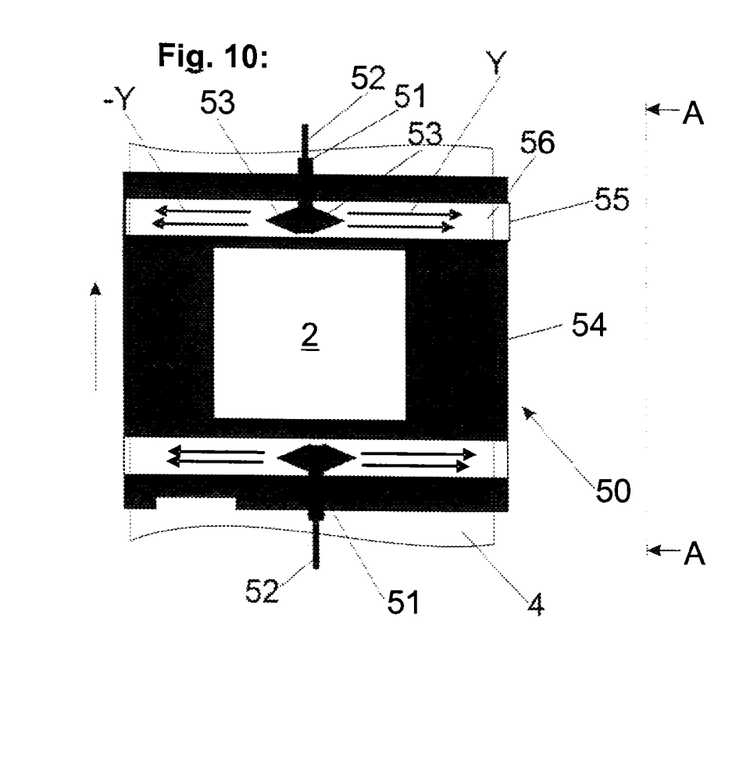

FIG. 10 shows a variant of a counter support, as for example illustrated in FIG. 10, and marked with the reference character 12. The counter support and/or monitoring station shown here are marked with the reference character 50. The material web 4 is guided in the travel direction z over this monitoring station 50. Furthermore, pipelines 51 embodied as T-parts are discernible, by which a supplied pressurized air flow, indicated with the arrow 52, is divided into two partial flows which are thus deflected by 90° each. Instead of T-parts, for example two separate pipes which only deflect the air may be provided here, already supplied with only partial air flows. One trained in the art should know other variants. The pipelines end in jets 53, from which the partial air flows exit in the directions Y and/or −Y, with these directions extending perpendicular in reference to the travel direction of the material web 4.

It must be observed that, advantageously, an above-described jet arrangement is beneficial both upstream as well as downstream in reference to the measuring background 2 so that the web 4 can also contact the measuring background over the entire area if possible and/or shows a contact to this as constant as possible in order to prevent any falsified measurements.

The jets 53 are preferably arranged in the center of the channels 56, which show openings 55 at the edges 54 of the station 50 such that the flowing air can escape unhindered into the environment so that a steady pressure difference is prevalent. This way steady measuring conditions develop so that measurements performed at different points of time can be compared to each other.

Another advantage of the station 50 to be mentioned is the fact that it shows a low influence at best upon measurements when the web [travels] in the direction Y or −Y, because the suction force caused by the Bernoulli effect should remain approximately constant.

Figure 11:
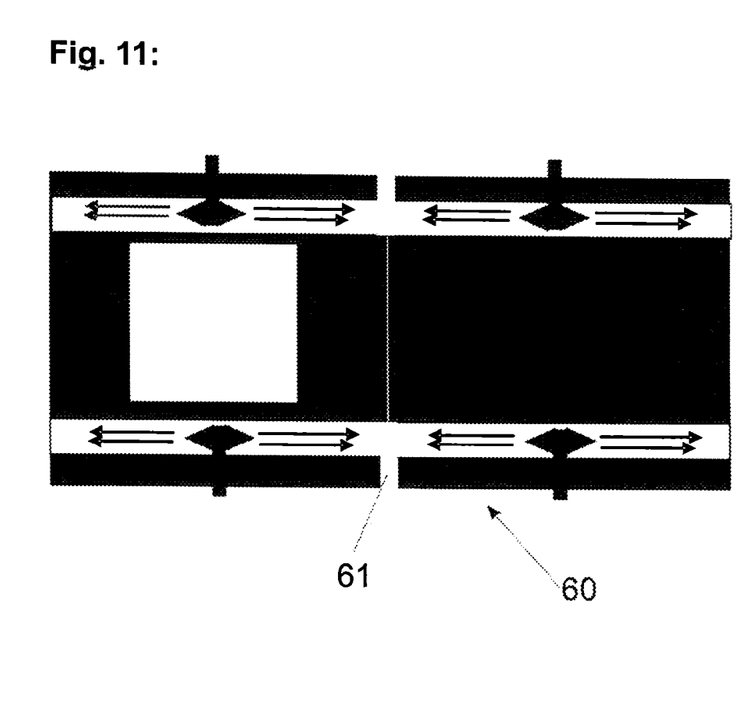

FIG. 11 shows another station 60, which is formed essentially from two stations 50 arranged next to each other, as shown in FIG. 10.

An important addition is here the fact that apertures 61 must be provided between these two partial stations, so that the air guided in the direction towards the boundary between the two partial stations can also escape unhindered into the environment. The elements of the station 60, equivalent to those of the station 50, have not been marked with reference characters. It is to be observed, though, that the station 60 comprises two different measuring backgrounds 2, which, depending on the properties of the material web (consistency, light permeability, etc.), can be used to perform measurements. For this purpose the material web 4 can be deflected over the respective partial section of the station 60. Matching deflection devices may be provided. However, it may also be provided to embody the stations 60 in a displaceable fashion in the direction Y or −Y via a displacement device.

Figure 12:
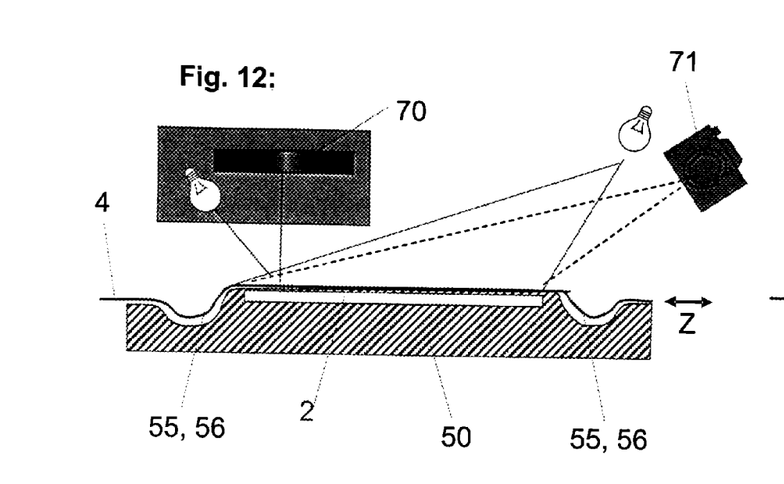

FIG. 12 shows the detail A-A of FIG. 10. In this example the measuring background 2 is arranged elevated in reference to the virtual straight traveling path of the web 4 so that the latter also rests on the measuring background as flat as possible. The edges 57 may be beveled, as shown. Ideally their profile is adjusted to the expected web travelling path such that the web, which may travel with considerable speed, is not disturbed. At high transportation speed the edges 57 might otherwise lead to the web forming standing waves above the measuring background so that no reliable measurements are possible.

In the exemplary embodiment according to FIG. 12, the measuring background 2 serves both for measuring with a spectral-photometer 70 as well as measuring with an imaging or densiometric sensor 71, for example a camera.

Figure 13:
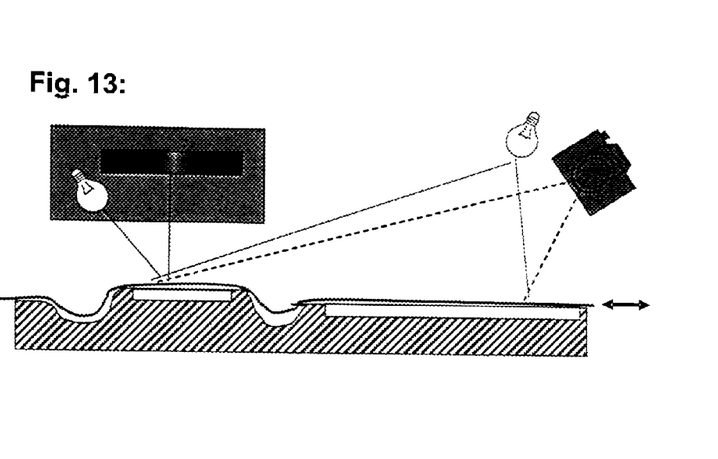
FIG. 13 A variant of FIG. 12

In the exemplary embodiment according to FIG. 13, contrary to the example according to FIG. 12, two measuring backgrounds are provided, one for each photometer and/or for each sensor 70, 71.

Figure 14:
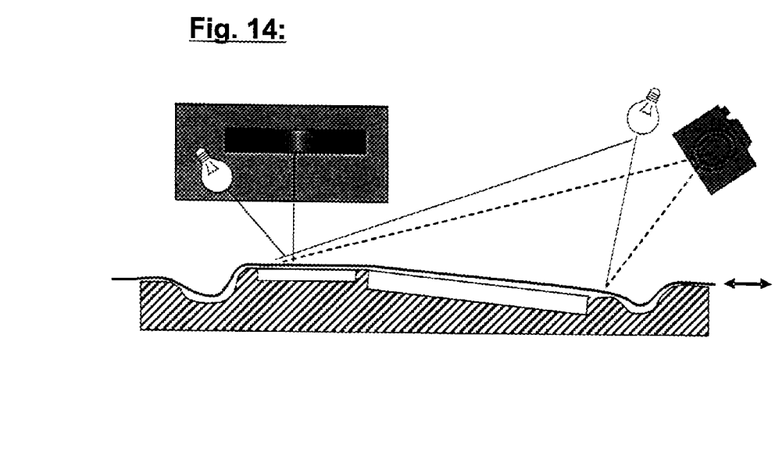
FIG. 14 Another variant of FIG. 12
Figure 15:
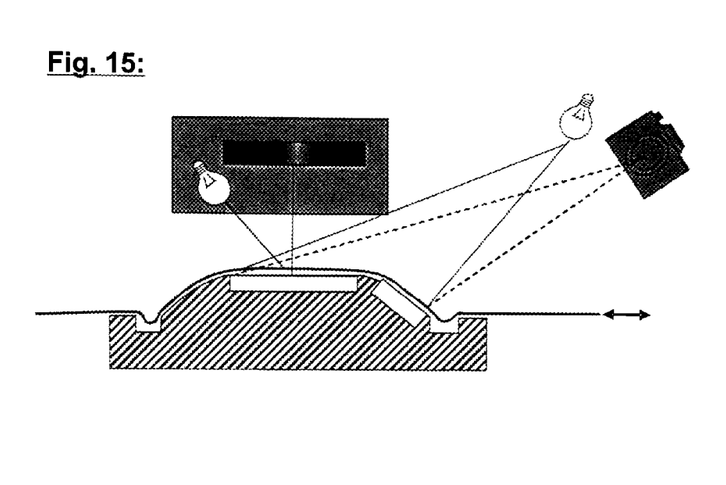
FIG. 15 Another variant of FIG. 12

The exemplary embodiments according to FIGS. 14 and 15 show additional arrangements of the measuring backgrounds. In FIG. 14 the separate measuring background for the sensor 71 is arranged descending in the travel direction z, with the end of the level of the straight virtual web progression falling short, which would be present if no station was provided.

In FIG. 15 the elevated arrangement of the measuring background is selected such that the measuring background for the sensor 71 arranged in a descending fashion no longer falls short of the straight extending web. All arrangements may show advantages, depending on the features of the material web 4.

In FIGS. 12 to 15 respectively identical elements are marked with reference characters in one figure only. They apply however also for the other figures.

In the present patent application, numerous exemplary embodiments of the invention have been explained. Combinations of these exemplary embodiments are also possible and explicitly provided, even if they are not explicitly described. Thus, they are also included in the scope of the disclosure of this application.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

| List of reference characters | |
|---|---|
| 1 | First station for monitoring a material web |
| 2 | First counter support/measuring background |
| 3 | First sensor |
| 4 | Material web/web |
| 5 | Master roller |
| 6 | First compressed air jet |
| 7 | Second compressed air jet |
| 8 | Guide roller |
| 9 | Traverse |
| 10 | |
| 11 | Second station for monitoring a material web |
| 12 | Second counter support/measuring background |
| 13 | Second sensor |
| 14 | Bright field illumination |
| 15 | Dark field illumination |
| 16 | Light cone |
| 17 | Guide roller |
| 18 | Background illumination |
| 19 | Arrow in the pivotal direction of the counter supports 32 and 22 |
| 20 | Counter support system |
| 21 | |
| 22 | White roller |
| 23 | |
| 24 | |
| 30 | |
| 31 | |
| 32 | Counter support |
| 33 | First surface of the counter support 32 |
| 34 | Reflector |
| 35 | Second surface of the counter support 32 |
| 36 | Arrows (air outlet from the counter support 32) |
| 37 | Pressure-resistant housing of the counter support 32 |
| 38 | Channel/pipe for compressed air |
| 39 | Background illumination of the counter support 32 |
| 40 | |
| 41 | Station for monitoring a material web |
| 42 | |
| 43 | |
| 50 | |

What is claimed is:

1. A machine for printing a material web, said machine comprising:
   a station for monitoring the printed material web,
   the station including a sensor for monitoring the material web and at least one counter support for guiding the material web, with the at least one counter support being located on a side of the web facing away from the sensor; and
   a device with which a pressure difference can be generated and which is installed such that a force results acting upon the material web in a direction towards the at least one counter support,
   the device, arranged at a side of the material web facing away from the sensor, which generates a vacuum, including jets from which air flows can be guided out, pressurized, and aligned perpendicular to a travel direction (z) of the material web, with the jets of the device being arranged upstream and downstream from the counter support in the travel direction of the material web,
   the device being an apparatus having the jets for providing blow air, with the provided blow air having a flow rate exceeding a traveling speed of the material web,
   with the jets being arranged (i) in directions perpendicular relative to the travel direction (z) such that the blow air assumes a direction of flow essentially extending perpendicular relative to the travel direction (z) and (ii) in channels arranged perpendicularly in the counter support relative to the travel direction (z).

2. The machine according to claim 1, wherein the jets are arranged in a middle of the channels and generate flows aligned in a direction towards sides of the counter support.

3. The machine according to claim 1, wherein a surface of the counter support facing the material web is embodied evenly in an area of the station.

4. The machine according to claim 1, wherein a surface of the counter support facing the material web is white in an area of the station.

5. The machine according to claim 1, wherein a surface of the counter support facing the material web has a material of construction that is a smooth, homogenous material in an area of the station.

6. The machine according to claim 1, wherein a surface of the counter support facing the material web includes Teflon in an area of the station.

7. The machine according to claim 1, wherein a surface of the counter support facing the material web includes microporous Teflon in an area of the station.

8. The machine according to claim 1, wherein the sensor is a spectral sensor.

9. The machine according to claim 1, further comprising a displacement device, with which the surface of the counter support facing the material web can be displaced in an area of the station perpendicular (x) relative to the travel direction (z) of the material web.

10. The machine according to claim 1, wherein the station includes at least one second sensor, with which the side of the material web facing the at least one second sensor can be monitored,
   with at least one second counter support being positioned opposite the at least one second sensor on the side of the material web facing away from the at least one second sensor,
   the at least one second counter support being provided with at least one of a white roller and a stationary counter support with an optic element, preferably a background illumination or a reflector.

11. The machine according to claim 10, wherein the stationary counter support can be made to contact the material web, and be separated from the material web.

12. The machine according to claim 11, wherein the surface of the stationary counter support facing the material web in the web travel direction (z) upstream and/or downstream relative to the optic element has a material of construction that is a porous or perforated material, preferably micro-porous Teflon.

13. The machine according to claim 10, further comprising at least two illumination devices, with which the monitoring area of the at least one second sensor can be illuminated.

14. A method of printing a material web, comprising:
monitoring a printed material web via a sensor in an area of a station for monitoring the material web from a first side thereof, and guiding the material web on a second side thereof by at least one counter support; and
generating a pressure difference with devices, with a resulting force acting upon the material web in a direction towards the counter support,
with a pressure being generated by a device, arranged at a side of the web facing away from the sensor and generating a vacuum, the device including jets from which an air flow can be guided out, subject to pressurization, and aligned perpendicular to a travel direction (z) of the material web, with the jets of the device being arranged upstream and downstream from the counter support relative to the travel direction of the material web,
the device being an apparatus having the jets for providing blow air, with the provided blow air having a flow rate exceeding a traveling speed of the material web,
with the jets being arranged (i) in directions perpendicular relative to the travel direction (z) such that the blow air assumes a direction of flow essentially extending perpendicular relative to the travel direction (z) and (ii) in channels arranged perpendicularly in the counter support relative to the travel direction (z).

15. The method according to claim 14, wherein at least one of a speed of the air flow and a volume of the air flow is adjusted such that no measurable air gap exists between the counter support and the material web.

16. The machine according to claim 10, wherein the at least one second sensor is a densiometric densitometric sensor.

* * * * *